United States Patent
Ludolph

(10) Patent No.: US 9,895,491 B2
(45) Date of Patent: *Feb. 20, 2018

(54) FIELD UPDATE OF AN AMBULATORY INFUSION PUMP SYSTEM

(71) Applicant: Tandem Diabetes Care, Inc., San Diego, CA (US)

(72) Inventor: Don Ludolph, Huntington Beach, CA (US)

(73) Assignee: Tandem Diabeters Care, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/995,958

(22) Filed: Jan. 14, 2016

(65) Prior Publication Data

US 2016/0129185 A1    May 12, 2016

Related U.S. Application Data

(63) Continuation of application No. 13/838,084, filed on Mar. 15, 2013, now Pat. No. 9,242,043.

(51) Int. Cl.
*G06F 19/00* (2011.01)
*G06F 9/44* (2006.01)
(Continued)

(52) U.S. Cl.
CPC ............ *A61M 5/172* (2013.01); *A61M 5/142* (2013.01); *A61M 5/1723* (2013.01); *G06F 8/65* (2013.01); *G06F 19/3406* (2013.01); *G06F 19/3412* (2013.01); *G06F 19/3468* (2013.01); *A61M 2005/14208* (2013.01);
(Continued)

(58) Field of Classification Search
CPC .... G06F 8/65; G06F 19/3412; G06F 19/3468; G06F 19/3406; G06F 19/3418; G06F 19/322; A61M 5/172; A61M 5/142; A61M 5/1723; A61M 2205/3584; G06Q 50/22; A61B 5/4833; A61B 5/14532; A61B 5/0008; A61B 5/0084; A61B 2562/08

See application file for complete search history.

(56) References Cited

U.S. PATENT DOCUMENTS

| | | |
|---|---|---|
| 4,731,051 A | 3/1988 | Fischell |
| 5,621,797 A | 4/1997 | Rosen |

(Continued)

FOREIGN PATENT DOCUMENTS

| | | | |
|---|---|---|---|
| WO | WO 2007065944 A1 | 6/2007 |
| WO | WO 2009032400 A1 | 3/2009 |

OTHER PUBLICATIONS

Masci et al., Verification of interactive software for medical devices: PCA infusion pumps and FDA regulation as an example, Jun. 2013, 10 pages.*

(Continued)

*Primary Examiner* — Thuy Dao
(74) *Attorney, Agent, or Firm* — Patterson Thuente Pedersen, P.A.

(57) ABSTRACT

Portable or ambulatory infusion devices and systems capable of remotely updating an ambulatory fluid delivery device include safety protocols that verify the status of the ambulatory fluid delivery device before and after a field update of software. Methods of accomplishing the same field update of software are also described.

20 Claims, 3 Drawing Sheets

(51) Int. Cl.
*A61B 5/00* (2006.01)
*H04L 29/08* (2006.01)
*A61M 5/172* (2006.01)
*A61M 5/142* (2006.01)
*G06F 9/445* (2018.01)

(52) U.S. Cl.
CPC . *A61M 2205/18* (2013.01); *A61M 2205/3569* (2013.01); *A61M 2205/3584* (2013.01); *A61M 2205/502* (2013.01); *A61M 2205/52* (2013.01); *A61M 2205/60* (2013.01); *A61M 2230/005* (2013.01); *A61M 2230/20* (2013.01); *A61M 2230/201* (2013.01); *A61M 2230/30* (2013.01); *A61M 2230/50* (2013.01); *A61M 2230/63* (2013.01)

(56) References Cited

U.S. PATENT DOCUMENTS

| | | |
|---|---|---|
| 5,704,366 A | 1/1998 | Tacklind et al. |
| 5,935,099 A | 8/1999 | Peterson et al. |
| 6,039,251 A | 3/2000 | Holowko et al. |
| 6,241,704 B1 | 6/2001 | Peterson et al. |
| 6,248,067 B1 | 6/2001 | Causey, III et al. |
| 6,360,888 B1 | 3/2002 | Mcivor et al. |
| 6,363,282 B1 | 3/2002 | Nichols et al. |
| 6,442,433 B1 | 8/2002 | Linberg |
| 6,475,180 B2 | 11/2002 | Peterson et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,564,104 B2 | 5/2003 | Nelson et al. |
| 6,635,014 B2 | 10/2003 | Starkweather et al. |
| 6,641,533 B2 | 11/2003 | Causey, III et al. |
| 6,694,191 B2 | 2/2004 | Starkweather et al. |
| 6,718,547 B2 | 4/2004 | Takeo |
| 6,740,059 B2 | 5/2004 | Flaherty |
| 6,749,587 B2 | 6/2004 | Flaherty |
| 6,768,425 B2 | 7/2004 | Flaherty et al. |
| 6,809,653 B1 | 10/2004 | Mann et al. |
| 6,872,200 B2 | 3/2005 | Mann et al. |
| 6,936,029 B2 | 8/2005 | Mann et al. |
| 6,979,326 B2 | 12/2005 | Mann et al. |
| 6,997,920 B2 | 2/2006 | Mann et al. |
| 7,025,743 B2 | 4/2006 | Mann et al. |
| 7,029,455 B2 | 4/2006 | Flaherty |
| 7,098,803 B2 | 8/2006 | Mann et al. |
| 7,109,878 B2 | 9/2006 | Mann et al. |
| 7,137,964 B2 | 11/2006 | Flaherty |
| 7,181,505 B2 | 2/2007 | Haller et al. |
| 7,324,012 B2 | 1/2008 | Mann et al. |
| 7,324,949 B2 | 1/2008 | Bristol |
| 7,347,836 B2 | 3/2008 | Peterson et al. |
| 7,383,358 B1 | 6/2008 | Kennedy |
| 7,390,458 B2 | 6/2008 | Burow et al. |
| 7,602,310 B2 | 10/2009 | Mann et al. |
| 7,647,237 B2 | 1/2010 | Malave et al. |
| 7,654,976 B2 | 2/2010 | Peterson et al. |
| 7,717,903 B2 | 5/2010 | Estes et al. |
| 7,774,038 B2 | 8/2010 | Wang et al. |
| 7,815,602 B2 | 10/2010 | Mann et al. |
| 7,819,843 B2 | 10/2010 | Mann et al. |
| 7,837,651 B2 | 11/2010 | Bishop et al. |
| 7,860,583 B2 | 12/2010 | Condurso et al. |
| 7,875,022 B2 | 1/2011 | Wenger et al. |
| 7,877,489 B2 | 1/2011 | Salesky et al. |
| 7,928,850 B2 | 4/2011 | Hayter et al. |
| 7,942,844 B2 * | 5/2011 | Moberg ............... A61M 5/142 604/65 |
| 7,955,843 B2 | 6/2011 | Barringer, Jr. |
| 7,999,674 B2 | 8/2011 | Kamen |
| 8,002,700 B2 | 8/2011 | Ferek-Petric et al. |
| 8,032,226 B2 | 10/2011 | Miller et al. |
| 8,051,414 B2 | 11/2011 | Stender |
| 8,065,161 B2 | 11/2011 | Howard et al. |
| 8,078,983 B2 | 12/2011 | Davis et al. |
| 8,109,921 B2 | 2/2012 | Estes et al. |
| 8,118,770 B2 | 2/2012 | Galley et al. |
| 8,149,131 B2 | 4/2012 | Blomquist |
| 8,202,267 B2 | 6/2012 | Field et al. |
| 8,206,350 B2 | 6/2012 | Mann et al. |
| 8,209,060 B2 * | 6/2012 | Ledford ............... A61M 5/1452 604/151 |
| 8,219,982 B2 | 7/2012 | Harkanyi et al. |
| 8,225,015 B2 | 7/2012 | Gao-Saari et al. |
| 8,234,128 B2 | 7/2012 | Martucci et al. |
| 8,239,852 B2 | 8/2012 | Etchegoyen |
| 8,249,683 B2 | 8/2012 | Wang et al. |
| 8,275,438 B2 | 9/2012 | Simpson et al. |
| 8,285,328 B2 | 10/2012 | Caffey et al. |
| 8,287,495 B2 | 10/2012 | Michaud et al. |
| 8,294,581 B2 | 10/2012 | Kamen |
| 8,323,188 B2 | 12/2012 | Tran |
| 8,337,469 B2 | 12/2012 | Eberhart et al. |
| 8,337,486 B2 | 12/2012 | Yodfat et al. |
| 8,340,792 B2 | 12/2012 | Condurso et al. |
| 8,380,536 B2 | 2/2013 | Howard et al. |
| 8,402,151 B2 | 3/2013 | Young |
| 8,414,563 B2 | 4/2013 | Kamen et al. |
| 8,435,206 B2 | 5/2013 | Evans et al. |
| 8,451,230 B2 | 5/2013 | Celentano et al. |
| 8,452,953 B2 | 5/2013 | Buck et al. |
| 8,465,460 B2 | 6/2013 | Yodfat et al. |
| 8,475,409 B2 | 7/2013 | Tsoukalis |
| 8,562,558 B2 | 10/2013 | Kamath et al. |
| 8,573,027 B2 | 11/2013 | Rosinko et al. |
| 8,579,853 B2 | 11/2013 | Reggiardo et al. |
| 8,595,607 B2 | 11/2013 | Nekoomaram et al. |
| 8,726,266 B2 | 5/2014 | Kiaie |
| 8,740,847 B2 | 6/2014 | Levesque et al. |
| 8,768,717 B2 | 7/2014 | Blomquist |
| 8,788,632 B2 | 7/2014 | Taylor |
| 8,952,794 B2 | 2/2015 | Blomquist |
| 8,954,336 B2 | 2/2015 | Blomquist |
| 8,986,253 B2 | 3/2015 | DiPerna |
| 8,992,475 B2 | 3/2015 | Mann |
| 9,135,393 B1 | 9/2015 | Blomquist |
| 9,242,043 B2 | 1/2016 | Ludolph |
| 9,381,302 B2 * | 7/2016 | Miller ................. G06F 19/3468 |
| 9,494,150 B2 * | 11/2016 | Gray ................. A61M 5/14224 |
| 9,675,756 B2 * | 6/2017 | Kamen ............. A61M 5/16859 |
| 9,764,087 B2 * | 9/2017 | Peterfreund ....... A61M 5/16827 |
| 2002/0029776 A1 | 3/2002 | Blomquist |
| 2002/0040208 A1 | 4/2002 | Flaherty et al. |
| 2002/0052539 A1 | 5/2002 | Haller et al. |
| 2002/0072733 A1 | 6/2002 | Flaherty |
| 2003/0095648 A1 | 5/2003 | Kaib |
| 2003/0212364 A1 | 11/2003 | Mann et al. |
| 2004/0010207 A1 | 1/2004 | Flaherty et al. |
| 2004/0073095 A1 | 4/2004 | Causey et al. |
| 2004/0204673 A1 | 10/2004 | Flaherty |
| 2004/0215278 A1 | 10/2004 | Stegink et al. |
| 2004/0235446 A1 | 11/2004 | Flaherty et al. |
| 2004/0260233 A1 | 12/2004 | Garibotto et al. |
| 2005/0022274 A1 | 1/2005 | Campbell et al. |
| 2005/0075685 A1 | 4/2005 | Forsberg et al. |
| 2005/0102669 A1 | 5/2005 | Marney |
| 2005/0171512 A1 | 8/2005 | Flaherty |
| 2005/0171513 A1 | 8/2005 | Mann et al. |
| 2005/0177395 A1 | 8/2005 | Blomquist |
| 2005/0182831 A1 * | 8/2005 | Uchida ................. G06F 15/177 709/220 |
| 2005/0240246 A1 | 10/2005 | Lee et al. |
| 2005/0246416 A1 | 11/2005 | Blomquist |
| 2005/0251227 A1 | 11/2005 | Khoo et al. |
| 2006/0202859 A1 | 9/2006 | Mastrototaro et al. |
| 2006/0235472 A1 | 10/2006 | Goetz et al. |
| 2006/0276857 A1 | 12/2006 | Forsberg et al. |
| 2007/0016449 A1 | 1/2007 | Cohen et al. |
| 2007/0033074 A1 | 2/2007 | Nitzan et al. |
| 2007/0066956 A1 | 3/2007 | Finkel |
| 2007/0118405 A1 | 5/2007 | Campbell et al. |
| 2007/0135866 A1 | 6/2007 | Baker et al. |

(56) References Cited

U.S. PATENT DOCUMENTS

| | | |
|---|---|---|
| 2007/0136098 A1 | 6/2007 | Smythe |
| 2007/0156033 A1 | 7/2007 | Causey, III et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0033402 A1 | 2/2008 | Blomquist |
| 2008/0033749 A1 | 2/2008 | Blomquist |
| 2008/0034323 A1 | 2/2008 | Blomquist |
| 2008/0065007 A1 | 3/2008 | Peterson et al. |
| 2008/0065016 A1 | 3/2008 | Peterson et al. |
| 2008/0071580 A1 | 3/2008 | Marcus et al. |
| 2008/0076969 A1 | 3/2008 | Kraft et al. |
| 2008/0126969 A1 | 5/2008 | Blomquist |
| 2008/0147004 A1 | 6/2008 | Mann et al. |
| 2008/0147050 A1 | 6/2008 | Mann et al. |
| 2008/0249470 A1 | 10/2008 | Malave et al. |
| 2009/0018779 A1 | 1/2009 | Cohen et al. |
| 2009/0030733 A1 | 1/2009 | Cohen et al. |
| 2009/0042552 A1 | 2/2009 | Coppinger et al. |
| 2009/0069745 A1 | 3/2009 | Estes et al. |
| 2009/0069785 A1 | 3/2009 | Miller et al. |
| 2009/0085768 A1 | 4/2009 | Patel et al. |
| 2009/0150186 A1 | 6/2009 | Cohen et al. |
| 2009/0150865 A1 | 6/2009 | Young et al. |
| 2009/0170056 A1 | 7/2009 | Nam et al. |
| 2009/0177991 A1 | 7/2009 | Davis et al. |
| 2010/0010647 A1 | 1/2010 | Schroeder et al. |
| 2010/0023582 A1 | 1/2010 | Pedersen et al. |
| 2010/0031245 A1 | 2/2010 | Meller et al. |
| 2010/0063844 A1 | 3/2010 | Reinke |
| 2010/0130933 A1 | 5/2010 | Holland et al. |
| 2010/0146300 A1 | 6/2010 | Brown |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0168539 A1 | 7/2010 | Palerm et al. |
| 2010/0174553 A1 | 7/2010 | Kaufman et al. |
| 2010/0198034 A1 | 8/2010 | Thomas et al. |
| 2010/0198183 A1 | 8/2010 | Lanigan et al. |
| 2010/0228186 A1 | 9/2010 | Estes et al. |
| 2010/0234708 A1 | 9/2010 | Buck et al. |
| 2010/0274592 A1 | 10/2010 | Nitzan et al. |
| 2010/0277119 A1 | 11/2010 | Montague et al. |
| 2010/0286653 A1 | 11/2010 | Kubel et al. |
| 2010/0292556 A1 | 11/2010 | Golden |
| 2010/0324853 A1 | 12/2010 | Wang et al. |
| 2011/0004188 A1 | 1/2011 | Shekalim |
| 2011/0009824 A1 | 1/2011 | Yodfat et al. |
| 2011/0028937 A1 | 2/2011 | Powers et al. |
| 2011/0040251 A1* | 2/2011 | Blomquist .......... A61M 5/1413 604/151 |
| 2011/0106318 A1 | 5/2011 | Ledford |
| 2011/0126188 A1 | 5/2011 | Bernstein et al. |
| 2011/0190694 A1 | 8/2011 | Lanier, Jr. et al. |
| 2011/0196248 A1 | 8/2011 | Grunwald |
| 2011/0209139 A1 | 8/2011 | Dominick et al. |
| 2011/0213225 A1 | 9/2011 | Bernstein et al. |
| 2011/0256024 A1 | 10/2011 | Cole et al. |
| 2011/0257591 A1 | 10/2011 | Nelson Konen et al. |
| 2011/0265072 A1* | 10/2011 | Matthew .................. G06F 8/65 717/169 |
| 2011/0320595 A1 | 12/2011 | Konishi et al. |
| 2012/0016305 A1* | 1/2012 | Jollota ............... A61B 5/14532 604/151 |
| 2012/0022452 A1 | 1/2012 | Welsch et al. |
| 2012/0029433 A1 | 2/2012 | Michaud et al. |
| 2012/0029941 A1 | 2/2012 | Malave et al. |
| 2012/0059673 A1 | 3/2012 | Cohen et al. |
| 2012/0096451 A1* | 4/2012 | Tenbarge ............ G06F 11/1433 717/170 |
| 2012/0165614 A1 | 6/2012 | Strickland et al. |
| 2012/0185267 A1 | 7/2012 | Kamen et al. |
| 2013/0012878 A1 | 1/2013 | Blomquist |
| 2013/0018315 A1 | 1/2013 | Blomquist |
| 2013/0053816 A1 | 2/2013 | DiPerna et al. |
| 2013/0104120 A1 | 4/2013 | Arrizza et al. |
| 2013/0142367 A1 | 6/2013 | Berry |
| 2013/0159456 A1 | 6/2013 | Daoud et al. |
| 2013/0211854 A1 | 8/2013 | Wagstaff |
| 2013/0231711 A1 | 9/2013 | Kaib |
| 2013/0253600 A1 | 9/2013 | Drew et al. |
| 2013/0254332 A1 | 9/2013 | Stempfer |
| 2013/0268890 A1 | 10/2013 | Jensen et al. |
| 2013/0289657 A1 | 10/2013 | Rodriguez |
| 2013/0345625 A1 | 12/2013 | Causey, III |
| 2014/0033002 A1 | 1/2014 | Nekoomaram et al. |
| 2014/0039455 A1 | 2/2014 | Miller et al. |
| 2014/0054883 A1 | 2/2014 | Lanigan et al. |
| 2014/0094744 A1 | 4/2014 | Blomquist |
| 2014/0094764 A1 | 4/2014 | Blomquist |
| 2014/0095485 A1 | 4/2014 | Blomquist |
| 2014/0095499 A1 | 4/2014 | Blomquist |
| 2014/0163919 A1* | 6/2014 | Manigel ................ A61M 5/172 702/123 |
| 2014/0351712 A1 | 11/2014 | Blomquist |
| 2015/0052511 A1 | 2/2015 | Kiaie |
| 2015/0143356 A1 | 5/2015 | Charlton |
| 2015/0154369 A1 | 6/2015 | Blomquist |
| 2015/0157788 A1 | 6/2015 | Gescheit et al. |
| 2015/0317437 A1 | 11/2015 | Daoud et al. |
| 2015/0328396 A1 | 11/2015 | Adams et al. |
| 2016/0147978 A1 | 5/2016 | Adams et al. |

OTHER PUBLICATIONS

Kim et al., Safety-assured development of the GPCA infusion pump software, Oct. 2011, 10 pages.*

PCT Search Report and Written Opinion dated Jun. 5, 2014 for PCT Application No. PCT/US2014/021125 filed Mar. 6, 2014, 12 pages.

Application and File history for U.S. Appl. No. 13/838,084, filed Mar. 15, 2013. Inventor: Ludolph.

Masci et al., Verification of interactive software for medical devices: PCA infusion pumps and FDA regulation as an example, Jun. 2013, 10 pages.

N. Hrgarek, Certification and regulatory challenges in medical device software development, Jun. 2012, 4 pages.

Search Report dated Jul. 28, 2016 for EP Application No. 14768180. 3, 9 pages.

* cited by examiner

FIELD UPDATE OF AN AMBULATORY INFUSION PUMP SYSTEM

RELATED APPLICATION

This application is a continuation of application Ser. No. 13/838,084 filed Mar. 15, 2013, which is hereby fully incorporated herein by reference.

FIELD OF THE INVENTION

The present invention is directed to the remote updating of information and data within portable medical devices, such as infusion devices and related systems, including methods of performing such updates. In some cases, the devices and systems may be used for infusing a medicament, including fluid medicaments such as insulin, into a patient.

BACKGROUND

As the number of patients who are treated with ambulatory medical devices increases, so does the need for a facile and reliable way to update and verify the operation of such systems. Examples of ambulatory medical devices include, e.g., cardiac pacemakers, cardioverter defibrillators, neurostimulators (for treatment of, e.g., Parkinson's Disease, epilepsy, and for pain management) and fluid infusion pumps, such as those for the treatment of chronic conditions such as diabetes. In the case of non-implantable devices such as ambulatory infusion pumps, requesting that a patient send his or her pump to a servicing facility may leave the patient without the same level of care while the pump software, for example, is updated and may become costly when numerous pumps need to be updated. Likewise, sending a skilled service provider such as a field service representative (typically from the device manufacturer) to a user's location to update the software on a pump may be efficient when dealing with a convenient number of pumps in a relatively small location. However, as the number of ambulatory infusion pumps in the field increases, and their usage becomes more wide-spread, administering software updates through visits by a skilled service provider may become cumbersome, time-consuming and costly. Additionally, setting aside the time to meet with a skilled service provider may deter some patients from updating the software on their ambulatory infusion pump.

SUMMARY

Provided herein is an ambulatory fluid device that includes a user interface, a liquid drug repository, a pump, an electrical controller, a digital storage component, and a signal processing component. The user interface of the ambulatory fluid delivery device is one which a user operates to input directions and data that determine the dosing of a medicament to a patient. The liquid drug repository contains the medicament. The pump is fluidly connected to the liquid drug repository and configured to prevent accidental release of the medicament from the drug repository, and the electrical controller is configured to direct the pump to release the medicament according to a dosing profile and additional instructions from the user interface. The digital storage component is operably connected to the electrical controller and is configured to store, for example, data regarding the administered doses, device history logs of the fluid delivery device, the operating system of the fluid delivery device, user profile information and identifying information regarding the fluid delivery device and safety protocols for the fluid delivery device. The signal processing component sends and receives electrical data to and from the controller. The fluid delivery device can be configured to receive software updates sent from a qualified source, verify the appropriateness of the software updates for the fluid delivery device based upon the identifying information and device history logs, automatically install the software updates, update the device history logs and perform tests conforming to the safety protocols after installation of the software.

In various embodiments, the software updates may be received after the user requests the software update or may be automatically received by the ambulatory fluid delivery device. The software updates may be only installed after verifying that the ambulatory fluid delivery device is in a safe condition for update. In some such embodiments, the safe condition for update may include not currently administering the medicament, not being attached to the patient, the liquid drug repository not being in fluid communication with the patient, not containing any medicament, or any combination thereof. In some embodiments, the ambulatory fluid delivery device may further include an alarm system that indicates at least one of the start and the finish of the software update installation. In various embodiments, the signal processing component may include a wireless connection means for sending in receiving digital signals, a physical port for connecting cables to a computer or other device, or both a wireless connection means and a physical port. The ambulatory fluid delivery device can be configured to display interactive verification tests on the user interface prior to installing the software updates. In such devices, the verification tests can include tests to verify proximity to a source of the software updates, the willingness of the user to initiate the software updates, or both.

In a related aspect, a system for safely administering a medication to a patient that includes the ambulatory fluid delivery device described above and a central computing system is provided. The central computing system can exchange data, instructions, or both data and instructions, with the ambulatory fluid delivery device.

In various embodiments, the central computing system may exchange data that includes the device history logs of the ambulatory fluid delivery device, a patient basal medication dosage profile, patient information, or any combination thereof. The central computing system may verify the condition of the ambulatory fluid delivery device prior to sending software updates. In such embodiments, verifying the condition of the ambulatory fluid delivery device may include examining the device history logs for irregular device performance, retrieving the current status of the ambulatory fluid delivery device to ensure that it is in a safe configuration for update, verifying the amount of digital memory and other computing hardware parameters are suitable for the software updates, confirming that the software updates and existing software currently operating on the ambulatory fluid delivery device are compatible, or any combination thereof.

In some embodiments the system can further include a remote controller that communicates between the ambulatory fluid delivery device and the central computing system, a sensor system that communicates with the ambulatory fluid delivery device, the central computing system, or both the ambulatory fluid delivery device and the central computing system, an intermediate computing device that communicates between the ambulatory fluid delivery device and the central computing system, or any combination thereof.

In such embodiments, the remote controller may include a dedicated hand-held remote controlling device, a second ambulatory fluid delivery device, a portable computing device that is configured to communicate wirelessly with the ambulatory fluid delivery device, or any combination thereof.

In embodiments of the system that include a sensor system, the sensor system may include a continuous glucose monitoring system, a patient temperature monitoring system, a blood oxygen saturation monitoring system, a heart rate monitoring system, a blood pressure monitoring system, a patient activity monitoring system or any combination thereof. In embodiments of the system that include the intermediate computing device, the intermediate computing device may include a hand-held computing device, comprising a tablet, a personal digital assistant, a mobile phone, or any combination thereof, a desktop computer or a laptop computer. In various embodiments, the intermediate computing device can be a computing device configured to exchange data with the ambulatory fluid delivery device through a wireless connection and with the central computing system through the internet via a wired connection, a computing device configured to exchange data with the ambulatory fluid delivery device through a wireless connection and with the central computing system through a wireless connection comprising Wi-Fi, a cellular phone signal, or both, a computing device configured to exchange data with the ambulatory fluid delivery device and with the central computing system both via a wired connection, a computing device configured to exchange data with the ambulatory fluid delivery device through a wired connection and with the central computing system through the internet via a wireless connection comprising Wi-Fi, a mobile phone signal, or both, or any combination thereof.

In another embodiment, a method for remotely updating software on an ambulatory fluid deliver device is presented. The method can include interrogating the ambulatory fluid delivery device and obtaining data comprising a device history log from a central computing system. The method can also include the central computer system verifying that the ambulatory fluid delivery device has not exhibited unusual performance within a certain time period, verifying that the ambulatory fluid delivery device is compatible with a software update, verifying that a user of the ambulatory fluid delivery device wishes to update software on the ambulatory fluid delivery device, or any combination thereof. Additionally, the method can include sending the software update from the central computing system to the ambulatory fluid delivery device, confirming that the ambulatory fluid delivery device is in a safe condition for update, confirming that existing data on the ambulatory fluid delivery device is duplicated, performing the software update on the ambulatory fluid delivery device, verifying that the ambulatory fluid delivery device in is a safe condition for performance testing and that it performs as intended after the software update, and confirming that the duplicated, existing data on the ambulatory fluid delivery device is appropriately present on the ambulatory fluid delivery device.

In various embodiments, the method may further include prompting the user to configure the ambulatory fluid delivery device for regular operation. In such methods, regular operation may include the administration of one or more medications to a patient. A safe condition for update may include not currently administering a medicament, not being attached to a patient, a liquid drug repository not being in fluid communication with the patient, not containing any medicament, or any combination thereof. A safe condition for performance testing may include not currently administering a medicament, not being attached to a patient, a liquid drug repository not being in fluid communication with the patient, not containing any medicament, or any combination thereof.

In such embodiments, verifying that the ambulatory fluid delivery device performs as intended may include verifying the ability to dispense one or more medicaments, verifying the ability to update a device history log, verifying the ability of the ambulatory fluid delivery device to accept sensor data to influence medicament dosing, verifying the ability of the ambulatory fluid delivery device to repeatedly and safely perform dispensing actions or any combination thereof. Verifying that the ambulatory fluid delivery device has not exhibited unusual performance within a certain time period may include verifying the absence of error messages in the device history logs, examining the device history logs for unusual trends in deviation of actual dosage from intended dosage, or both. In some embodiments, verifying that the ambulatory fluid delivery device is compatible with a software update may include verifying the memory capacity of the ambulatory fluid delivery device, confirming that the model of the ambulatory fluid delivery device is compatible with the software update, or both. In some embodiments of the method, verifying that a user of the ambulatory fluid delivery device wishes to update software on the ambulatory fluid delivery device may include presenting the user with a message and accepting user input via a user interface on the ambulatory fluid delivery device, presenting the user with a message via a remote control and accepting user input via the remote control or via a user interface on the ambulatory fluid delivery device, presenting the user with a message via an external computing device and accepting user input via the external computing device or via a user interface on the ambulatory fluid delivery device; or any combination thereof.

In some embodiments, a method for remotely providing a software update for an ambulatory fluid delivery device is presented. The method can include interrogating the ambulatory fluid delivery device and obtaining data comprising a device history logs from a central computer system. The method can also include verifying that the ambulatory fluid delivery device has not exhibited unusual performance within a certain time period, verifying that the ambulatory fluid delivery device is compatible with a software update, verifying that a user of the ambulatory fluid delivery device wishes to update software on the ambulatory fluid delivery device, or any combination thereof. Additionally, the method can include sending the software update from the central computing system to the ambulatory fluid delivery device, confirming that the ambulatory fluid delivery device is in a safe condition for update, confirming that existing data on the ambulatory fluid delivery device is duplicated, receiving confirmation on the central computing system that the software update has occurred on the ambulatory fluid delivery device, receiving information verifying that the ambulatory fluid delivery device in is a safe condition for performance testing and that it performs as intended after the software update and receiving confirmation on the central computing system that the duplicated, existing data on the ambulatory delivery device is appropriately present on the ambulatory fluid delivery device.

Some embodiments include a method for remotely performing a software update on an ambulatory fluid delivery device. This method can include, in response to an interrogation from a central computing system, sending data comprising device history logs to the central computing system.

The method can also include receiving confirmation from the central computing system that the ambulatory fluid delivery device has not exhibited unusual performance within a certain time period, that the ambulatory fluid delivery device is compatible with the software update, that a user of the ambulatory fluid delivery device wishes to update software on the ambulatory fluid delivery device, or any combination thereof. Additionally, the method can include receiving the software update from the central computing system on the ambulatory fluid delivery device, confirming that the ambulatory fluid delivery device is in a safe condition for update via user input, sending existing data on the ambulatory fluid delivery device to the central computing system for duplication, sending confirmation from the ambulatory fluid delivery device that the software update has occurred on the ambulatory fluid delivery device, sending information from the ambulatory fluid delivery device verifying that the ambulatory fluid delivery device in is a safe condition for performance testing and that it performs as intended after the software update, and sending confirmation to the central computing system that the duplicated, existing data on the ambulatory fluid delivery device is appropriately present on the ambulatory fluid delivery device after the software update. Certain embodiments are described further in the following description, examples, claims and drawings. These features of embodiments will become more apparent from the following detailed description when taken in conjunction with the accompanying exemplary drawings.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Methods are described for updating an ambulatory medical device, including a portable fluid delivery device such as an infusion pump. The methods include, e.g., verification of the status of the ambulatory fluid delivery device or pump before and after the software update to decrease the likelihood of any unwanted or unintentional delivery of medicament or other errors of malfunctions.

Software Update System for an Ambulatory Medical Device

Figure 1:
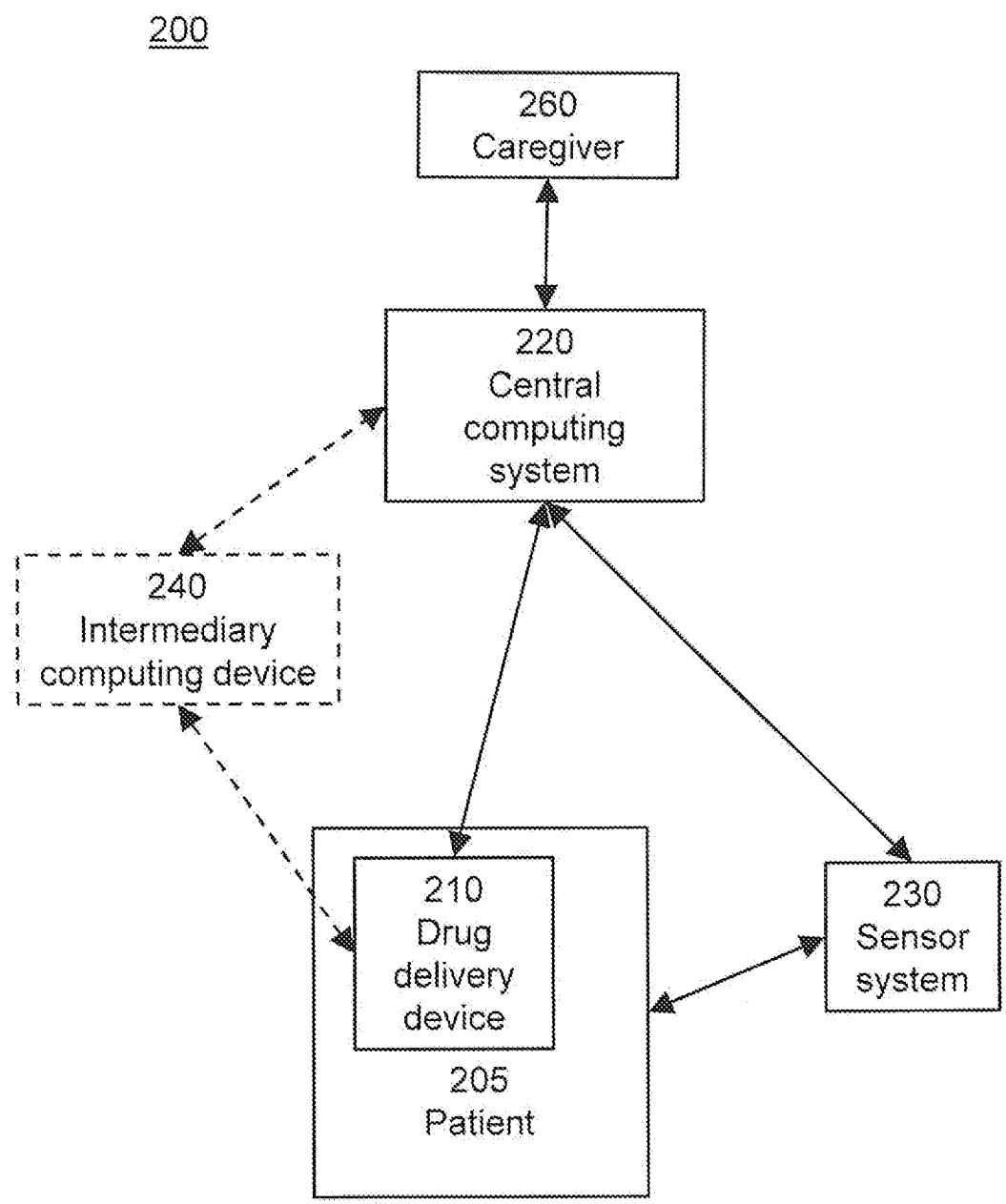
FIG. 1 is a schematic of an exemplary system for safely performing software updates on an ambulatory fluid delivery device such as an ambulatory infusion pump.

FIG. 1 shows a schematic of an exemplary system embodiment 200 for safely performing software updates on an ambulatory fluid delivery device, or pump 210. The system 200 includes an ambulatory fluid delivery device 210 that can administer medicament to a patient 205. The system 200 further includes a sensor system 230 coupled to the patient 205. The sensor system 230 may or may not be part of the ambulatory fluid delivery device or pump 210, and may provide data to the pump 210, or to a central computing system 220 independently, or both.

The fluid delivery device 210 and/or the sensor system 230 can be configured to communicate directly or indirectly (such as via an intermediary computing device 240) with a central computing system 220 that is accessible by a caregiver 260, such as a physician, nurse, etc. The caregiver 260 can access patient data from the central computing system 220, the patient data being obtained from the fluid delivery device 210. In some cases, the caregiver 260 may react to the patient data by interacting directly with the patient 200.

Examples of the types of software updates that may be performed include updates to the fluid delivery device's operating system, the firm ware, the communications protocols, the data encryption algorithms, the user interface, the device log, the device history record, and the like. For the purposes of the present disclosure, the term "software updates" may also include installation of the new software on the fluid delivery device and the removal of software from the fluid delivery device.

Software updates may be initiated by a user, such as a caregiver or a patient, by the fluid delivery device manufacturer or its representative, by the central computing system, or any combination thereof. The caregiver 260, if, e.g., properly prompted by the manufacturer of the pump 210, for instance, may cause the central computing system to provide software updates to the fluid delivery device 210 and/or provide care instructions to the fluid delivery device 210. Also, another entity, such as a manufacturer, authorized repair organization, distributor, or the like, may direct the central computing system 220 to provide software updates to the ambulatory fluid delivery device 210, either automatically as needed or upon prompting a user. Software updates may also be initiated automatically when the fluid delivery device 210 connects to an intermediary computing device 240 that is, in turn, connected to the central computing system 220. When an action, such as connecting the fluid delivery device 210 to an intermediary computing device 240, or an entity other than the patient initiates a software update, the fluid delivery device 210 may require input from the patient or a user before fully executing the software update.

Figure 2:
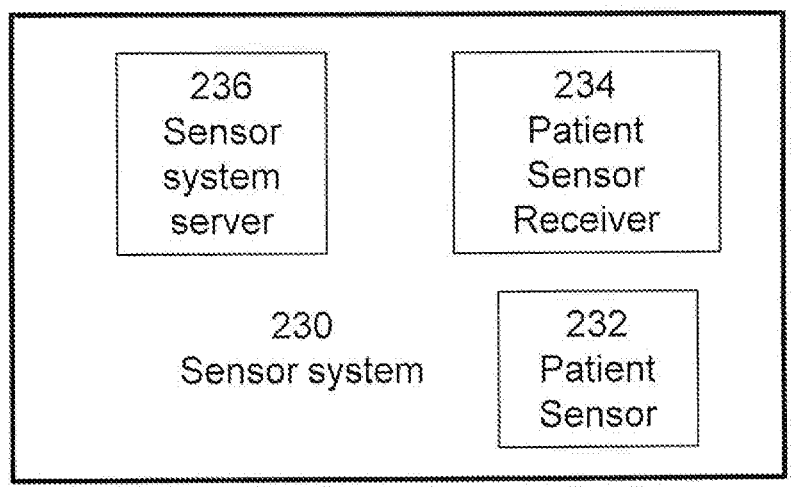
FIG. 2 depicts a schematic of an exemplary sensor system.

FIG. 2 shows a schematic diagram of the sensor system 230, which may include a patient status sensor 232, such as a glucose monitor. The sensor system 230 may also include components that permit the sensor system to communicate with the central computing system 220, such as a patient sensor receiver 234, and a sensor system server 236. Systems that may be part of the sensor systems 230 include, for example, a continuous glucose monitoring system; a patient temperature monitoring system; a blood oxygen saturation monitoring system; a heart rate monitoring system; a blood pressure monitoring system; a patient activity monitoring system; and the like. In addition to sensor systems related to the status of a patient, sensor systems that indicate the status of the ambulatory fluid delivery device may be present. Such sensors may indicate, for example, whether a medicament-containing cartridge is inserted into the ambulatory fluid delivery device, whether infusion lines are connected to a patient, the amount of medicament within the ambulatory fluid delivery device, the operational status of the systems and/or subsystems of the fluid delivery device, including but not limited to the hardware and/or software thereof, and the like.

The fluid delivery device 210 and sensor system 230 are configured to exchange the patient data with one another and with the central computing system 220. The type of patient data may vary and may include patient status data, such as glucose levels, heart rate, temperature, blood pressure, activity level; as well as delivered medicament data; insulin on board; and personal data (appropriately de-identified for privacy requirements, as necessary) such as patient name, sex, age, weight, and the like. The data exchange can occur directly between the fluid delivery device 210 and the computing system 220 or can occur between the sensor system 230 and the computing system 220. The patient data can be used to confirm that any contact between the ambulatory fluid delivery device 210 and the central computing system 220 is appropriate and that a software update from the central computing system to the fluid delivery device may be completed safely, as described further below.

Communication between the components of the system 200 may vary and may include wireless or wired connections and may occur over the Internet. Wireless communication may include any suitable wireless system, such as Bluetooth, Wi-Fi, radio frequency, Zigbee communication protocols, infrared or other optical systems, mobile phone systems, and the like. Wired connections can include telephone line connections, RS22 connection, standard USB and micro-USB connections, firewire connections, proprietary connections, or any other suitable type of wired connection.

Additionally, communication between and/or among the ambulatory fluid delivery device 210, sensor system 230 and central computing system 220 may be direct or it may be through another device, such as a remote controller or an intermediary computing device 240. A remote controller may include a dedicated hand-held remote controlling device, a second ambulatory fluid delivery device, a portable computing device that is configured to communicate wirelessly with the ambulatory fluid delivery device, monitors such as blood glucose monitors (including continuous blood glucose monitors), other suitable devices that allow a user to send instructions to the ambulatory fluid delivery device, or any combination thereof.

The intermediary computing device 240 may include, for example: a hand-held computing device, such as a tablet, a personal digital assistant, a mobile phone, phone, smartphone, personal digital assistant (PDA), a desktop computer, a laptop computer, and the like. The intermediary computing device may be configured to exchange data with the ambulatory fluid delivery device 210 through a wireless connection (including optical) and with the central computing system 220 through the internet via a wired connection. Alternatively, the intermediary computing device 240 may be configured to exchange data with the ambulatory fluid delivery device 210 through a wireless connection and with the central computing system 220 through a wireless connection comprising Wi-Fi, a mobile phone signal, or both. In other instances, the intermediary computing device 240 may be configured to exchange data with the ambulatory fluid delivery device 210 and with the central computing system 220 both through via a wired connection, or the intermediary computing device may 240 be configured to exchange data with the ambulatory fluid delivery device 210 through a wired connection and with the central computing system 220 through the internet or other network via a wireless connection comprising Wi-Fi, a mobile phone signal, or both. The inclusion of another device may allow for a smaller ambulatory fluid delivery device or for the inclusion of another device in the system, such as a sensor system.

The software update may include updates to the operating system, the firm ware, the communications protocols, the data encryption algorithms, the user interface, the device history logs, the device history record, and the like, of the fluid delivery device, as mentioned above. The software update may affect the power usage of the fluid delivery device. Additionally, the software update may improve the communications between the fluid delivery device and any of: the central computing system, sensory systems, intermediary computing device, and the patient. Improvement of communications may include establishing more secure signal pathways, creating quicker signal exchanges, or making messages more concise and understandable by the patient. Software updates may also coincide with hardware updates to the fluid delivery device, including changes to a disposable component of the fluid delivery device, such as a fluid-containing cartridge.

Verification of Ambulatory Fluid Delivery Device Status and Performance

Before and/or after a software update from the central computing system 220 to the fluid delivery device 210 is performed, at least a portion of the system 200 verifies the status of the ambulatory fluid delivery device 210 such as to verify that the ambulatory fluid delivery device 210 is in a proper operational state such that the pump will not harm the patient or otherwise malfunction or present problems as a result of a software update. A proper operational state may include one in which the device history logs indicate that the fluid delivery device 210 has not had deviations from expected performance, such as from expected dosage rates, for a threshold amount of time. It may be that the expected performance may be required to be maintained for the past week, the past month, or the past several months to be considered a proper operational state. The proper operational state may also include a requisite level of charge to be present in a battery or power level to be available from a power source. Free, unobstructed movement of parts of the fluid delivery device may also be required in order for the proper operational state to exist, and certain levels of performance may also be required from the memory, user interface, communications components, sensory systems, and the like in order for the fluid delivery device to be in the proper operational state.

The ambulatory fluid delivery 210 device participates in verification by sending patient data to the central computing system 220. The patient data helps to determine the suitability of the software update for the fluid delivery device 210 and may include, for example, the device history logs of the fluid delivery device, data regarding the administered doses, the operating system of ambulatory fluid delivery device, user profile information, and any other data that may be used determine whether the ambulatory fluid delivery device is suitable for the proposed software update.

The central computing system sends requests for data both before and after the software update, as well as sending the software update, when the system determines that the software update is compatible with the intended ambulatory fluid delivery device. Both the central computing system 220 and the ambulatory fluid delivery device 210 can verify that communication regarding the software update is occurring with a qualified source before transmitting the verification information described above. To verify that communication is occurring with a qualified source, the central computing system 220 can verify, for example, the serial number or model of the intended ambulatory fluid delivery device. On the ambulatory fluid delivery device end, a password or certificate may be transmitted to aid in verifying the communication source. Other secure processing protocols and/or hardware/firmware/software may be utilized, including encrypted communication protocols, secure processors, etc., as are known in the art may be used as desired between and among the various components and entities described herein.

The software update protocol can trigger, for example, the ambulatory fluid delivery device to confirm with a user that the connection between the patient and the fluid delivery device is in a safe condition with respect to the patient. A "safe condition" may be, for example, that the patient cannot accidentally receive unintentional amounts of medicament. Such conditions may include those when the ambulatory fluid delivery system is not currently administering the medicament, not attached to the patient, when the cartridge is not located within the ambulatory fluid delivery device, when the liquid drug repository not in fluid communication with the patient, when the ambulatory fluid delivery device does not contain any medicament, or any combination thereof. When in the safe condition, the fluid delivery device may display a message to have alternative materials for delivery of the fluid normally delivered by the fluid delivery device on hand for the patient. The fluid delivery device may also display messages for verification of a battery level or a constant power supply prior to proceeding with the software update, as well as warning to disconnect the fluid delivery device from the body of the patient.

A safe condition may be verified in many ways. The ambulatory fluid delivery device may have sensors to verify that a safe condition exists. The ambulatory fluid delivery device may send an inquiry message to a user, such as by presenting a message on the graphical user interface, reciting an audio message, sending a message to an external device, or the like, to confirm that the fluid delivery device is in a safe condition. The ambulatory fluid delivery device may remind the user to maintain the safe condition until after test conforming to the safety protocols have been successfully performed after the installation of the software update. The fluid delivery device may require that a user confirm that the software update should proceed by requiring input from the user that includes the providing a number that is visible on the fluid delivery device only after a portion of the device is disengaged, for example, when a medicament containing cartridge is removed. The number may be a static number, or it may be a dynamic number that is synchronized with a number generator that is also available to the central computing system.

The tests conforming to the safety protocols may vary depending on the device and the nature of the software update. There may be some tests that are always performed by the ambulatory fluid delivery device, such as those tests that are performed after initial construction of the fluid delivery device and upon powering on of the ambulatory fluid delivery device. These self-tests may include those which confirm the software and hardware configuration of the fluid delivery device, confirm that any previously loaded configurations, settings, or other data were not unintentionally deleted, and that confirm that the fluid delivery device performs according to factory initialized, or reset, settings. The self-tests may reset certain values, such as insulin on board (IOB).

Communications between a fluid delivery device and a central computing system may include accessing data through a request sent from the fluid delivery device to the central computing system. Alternatively, communications may include data transfer over a computer network from the fluid delivery device to the central computing system via an uploader application executing at a host device, such as an intermediary computing device, such that the uploader application may authenticate the fluid delivery device, extracts a data log (e.g. device history record) from the authenticated fluid delivery device, and uploads the extracted data log to the central computing system. Additionally, access to data on the central computing system may be controlled such that access is automatically terminated such that an unattended, but previously authorized device, cannot be used to gain access. Such authenticated interactions may be helpful in maintaining the safety and privacy of patients.

More particulars regarding systems for communication between exemplary fluid delivery devices and systems that include a central server (i.e., a network data manager), including those which utilize an intermediary computing device may be found in U.S. patent application Ser. No. 13/564,188, titled, "Therapy Management System," filed Aug. 1, 2012, the disclosure of which is incorporated by reference in its entirety herein.

Following the installation of software on the ambulatory fluid delivery device 210, the fluid delivery device 210 will conduct tests to verify the data contained on the ambulatory fluid delivery device, as well tests to confirm that the ambulatory fluid delivery device performs according to safety protocols that help to ensure the safety of the patient using the device. Data from the ambulatory fluid delivery device may be redundantly stored, or backed-up, by the central computing system prior to the installation of a software update on the ambulatory fluid delivery device. Such backed-up data may include device history logs; the device history record; user profiles, including basal rate profiles; user information, such as, but not limited to, name, age, sex, location, and care giver information; and the like. After a software update installation finishes on an ambulatory fluid delivery device 210, the fluid delivery device 210 may send the data back to the central computing system for comparison to the backed-up data. This process may assure patients that basal rate profiles and other dosing instructions, as well as other important information, will not be unexpectedly affected by a software update.

An exemplary method of performing software updates on an ambulatory fluid delivery device while the device is in the field includes verification of the ambulatory fluid delivery device status and performance, both before and after a software update occurs. The ambulatory fluid delivery device will be confirmed to be in a safe configuration and will have a performance record that indicates the fluid delivery device is in proper working order before the software update occurs. After the software update occurs, the ambulatory fluid delivery device will be tested and proven to be in working order before being returned to service, dispensing medicament to a patient.

In an exemplary method, a central computing server and an ambulatory fluid delivery device exchange information (such as over the Internet or other computer network) to confirm that a communication interaction is appropriate before taking further action. This may include a confirmation that a secure communication connection is accessible between the two components.

Once it is confirmed that the central computing server and the ambulatory fluid delivery device have an allowable connection, the central computing server verifies that the ambulatory fluid delivery device can appropriately accept a proposed software update and that the ambulatory fluid delivery device is in a safe condition. As discussed above, any of a variety of conditions can be used as criteria for the existence of a safe condition.

The central computing server then sends the software update to the ambulatory fluid delivery device. This can occur, for example, over a network such as the Internet. The ambulatory fluid delivery device, in turn, receives and installs the software update. Prior to installing the software, the ambulatory fluid delivery device may again verify that a safe condition exists.

Upon completion of the software update installation, the ambulatory fluid delivery device performs one or more tests to confirm that it is in proper operating condition. A user, such as a patient or care giver, then places the properly functioning ambulatory fluid delivery device back into service, by, for example, attaching infusion lines to the patient, adding medicament to the ambulatory fluid delivery device, or installing a medicament containing cartridge.

Example Ambulatory Fluid Delivery Device

An example of an ambulatory fluid delivery or pump device is now described. It should be appreciated that the following description is an example and the actual configuration of the ambulatory fluid delivery or pump can vary. A detailed description of exemplary devices can be found in U.S. Pat. No. 8,287,495, which is incorporated by reference in its entirety herein. Further examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. Provisional Patent Application No. 61/655,883 and U.S. Provisional Patent Application No. 61/656,967, each of which is incorporated herein by reference.

Figure 3:
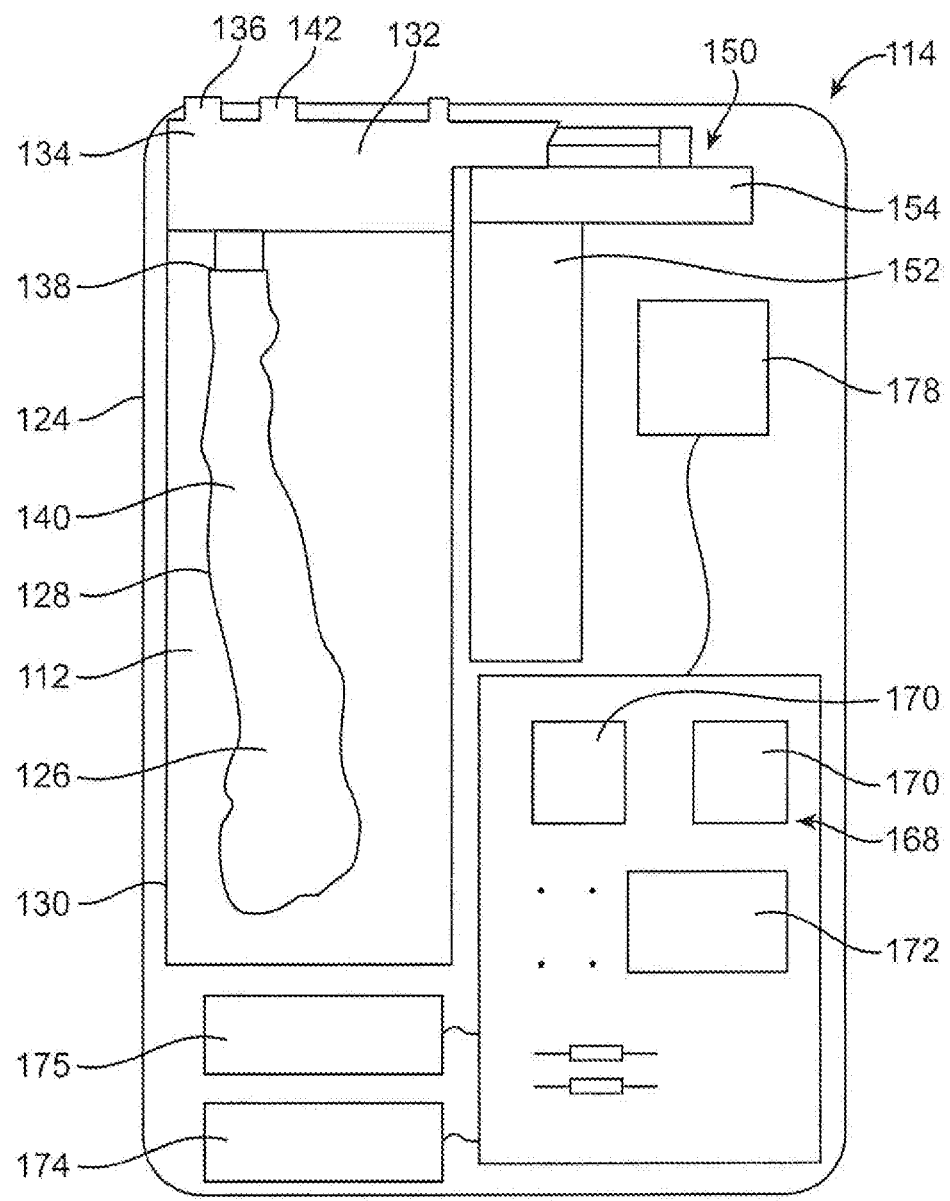
FIG. 3 is a schematic view of an interior of an exemplary ambulatory fluid delivery device such as an infusion pump.

FIG. 3 is a schematic view of an open housing 124 of an ambulatory fluid delivery device 114, such as a pump device. The exemplary ambulatory fluid delivery device 114 has within the housing 124 an area into which a cartridge 112 fits. The cartridge 112 has a substantially rigid container 130 that encloses a collapsible reservoir 126. The collapsible reservoir 126 is made of a flexible material or membrane 128 and that defines an interior volume 140. The cartridge 112 also includes a delivery mechanism 132, a fill port 134 with a re-sealable septum 136 sealed over the fill port 134, a reservoir inlet port 138 in fluid communication with the interior volume 140 of the collapsible reservoir 126, a fluid dispense port 142 in fluid communication with a bore 144 of the delivery mechanism 132, and a vent inlet port 146 and a vent outlet port 148, both in fluid communication with the bore 144. The collapsible reservoir 126 may have a bag-like structure with flexible walls that can collapse and expand depending upon the amount of material in the volume of the reservoir. The interior volume of the reservoir may be in fluid isolation from the remaining interior volume of the rigid container 130.

The cartridge 112 may be secured to the housing 124 of the ambulatory fluid delivery device 114 in releasable and operable manner. The housing 124 may be configured to house a drive mechanism 150 including a motor 152 and gear box 154 disposed in the housing 124. The drive mechanism 150 may be detachably and operatively coupled to the spool 156 member of the delivery mechanism 132. At least one pressure sensor may be disposed in a volume between an outside surface of the flexible material or membrane 128 of the collapsible reservoir 126 and an inside surface of the substantially rigid shell or case 130.

A graphic user interface (GUI) may be operatively coupled to a controller 168, which may include at least one processor 170, a memory device 172 and connective circuitry or other data conduits that couple the data generating or data managing components of the device. A power storage cell in the form of a battery 174 that may be rechargeable may also be disposed within the housing 124. Data generating or managing components of the device may include the processor(s) 170, the memory device 172, sensors, including any pressure or temperature sensors, the GUI and the like.

Other components such as the vibratory motor 175, speaker, battery 174 and motor 152 of the drive mechanism 150 may also be operatively coupled to the controller 168. Connective circuitry may include conductive wiring such as copper wiring, fiber optic conduits, RF conduits and the like. The controller 168 may include at least one processor 170 and a memory device 172, the controller 168 being operatively coupled to the drive mechanism 150, a GUI, and at least one pressure sensor. The controller may be configured to generate a signal to the drive mechanism 150 to displace the spool of the delivery mechanism 132 when dispensing medicament from the ambulatory fluid delivery device. The controller may also be configured to send and receive data to and from a central computing system.

Safe configurations in this exemplary ambulatory fluid delivery device 114 include ones in which the cartridge 112 is removed from the fluid delivery device 114, the reservoir 126 is empty, the fluid dispense port 142 is disconnected from any lines or tubing connected to an infusion site on a patient, and the like.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

The invention claimed is:

1. A method performed by software executable instructions on a hardware processor for remotely updating software on an ambulatory fluid delivery device comprising:
   from a computing system, interrogating the ambulatory fluid delivery device and obtaining data, from the ambulatory fluid delivery device, the data including a patient basal medication dosage profile and device history logs;
   by the computing system, verifying that the ambulatory fluid delivery device is compatible with a software update, including both verifying a memory capacity of the ambulatory fluid delivery device and confirming that a model of the ambulatory fluid delivery device is compatible with the software update;
   verifying that a user of the ambulatory fluid delivery device wishes to update software on the ambulatory fluid delivery device;
   sending the software update from the computing system to the ambulatory fluid delivery device;
   verifying that the ambulatory fluid delivery device is in a safe condition for the software update, including verifying an absence of error messages within a certain time period in the device history logs;
   performing the software update on the ambulatory fluid delivery device; and
   verifying that the ambulatory fluid delivery device in is a safe condition to perform as intended after the software update.

2. The method of claim 1, further comprising, by the computing system:
   receiving a password from the ambulatory fluid delivery device; and
   verifying the password received from the ambulatory fluid delivery device.

3. The method of claim 1, wherein the computing system includes a central computing system and an intermediate computing device, and further comprising, by the intermediate computing device, facilitating communications relating to the software update between the ambulatory fluid delivery device and the central computing system.

4. The method of claim 3, wherein the intermediate computing device comprises a portable computing device.

5. The method of claim 1, wherein the step of verifying that the ambulatory fluid delivery device is in a safe condition for the software update is performed prior to the step of sending the software update to the ambulatory fluid delivery device.

6. A system for remotely updating software operating on an ambulatory fluid delivery device, comprising:
   an ambulatory fluid delivery device; and
   a computing system having a hardware processor configured to remotely update software operating on the ambulatory fluid delivery device, wherein upon determining that a software update is available for the ambulatory fluid delivery device the hardware processor of the computing system is programmed to:
      interrogate the ambulatory fluid delivery device to obtain data from the ambulatory fluid delivery device, the data including a patient basal medication dosage profile and device history logs;
      verify that the ambulatory fluid delivery device is compatible with a software update, including both verifying a memory capacity of the ambulatory fluid delivery device and confirming that a model of the ambulatory fluid delivery device is compatible with the software update;
      verify that a user of the ambulatory fluid delivery device wishes to update software on the ambulatory fluid delivery device;
      send the software update to the ambulatory fluid delivery device;
         verify that the ambulatory fluid delivery device is in a safe condition for the software update, including verifying an absence of error messages within a certain time period in the device history logs;
         receive confirmation that the software update has occurred on the ambulatory fluid delivery device; and
         verify that the ambulatory fluid delivery device is in a safe condition to perform as intended after the software update.

7. The system of claim 6, wherein the central computing system is further programmed to:
   receive a password from the ambulatory fluid delivery device; and
   verify the password received from the ambulatory fluid delivery device.

8. The system of claim 6, wherein the computing system includes a central computing system and an intermediate computing device, the intermediate computing device configured to facilitate communications relating to the software update between the ambulatory fluid delivery device and the central computing system.

9. The system of claim 8, wherein the intermediate computing device comprises a portable computing device.

10. The system of claim 6, where a safe condition for the software update comprises one or more of:
    the ambulatory fluid delivery device not currently administering a medicament,
    the ambulatory fluid delivery device not being attached to a patient, and
    a liquid medicament repository not being in fluid communication with the patient.

11. The system of claim 6, wherein verifying that the ambulatory fluid delivery device is in a safe condition to perform as intended after the software update comprises one or more of:
    verifying an ability of the ambulatory fluid delivery device to dispense one or more medicaments;
    verifying an ability of the ambulatory fluid delivery device to update a device history log; and
    verifying an ability of the ambulatory fluid delivery device to accept sensor data to influence medicament dosing.

12. The system of claim 6, wherein verifying a user of the ambulatory fluid delivery device wishes to update software on the ambulatory fluid delivery device includes receiving an indication of user input accepting a message pertaining to the software update.

13. The system of claim 6, wherein the hardware processor of the computing system is programmed to verify that the ambulatory fluid delivery device is in a safe condition for the software update prior to sending the software update to the ambulatory fluid delivery device.

14. A system for remotely updating software operating on an ambulatory fluid delivery device, comprising;
    an ambulatory fluid delivery device;
    a central computing system having a hardware processor and located remotely from the ambulatory fluid delivery device; and
    an intermediate computing system having hardware processor configured to facilitate an update to software operating on the ambulatory fluid delivery device via the central computing system, wherein the intermediate computing device is programmed to:
  interrogate the ambulatory fluid delivery device to obtain data from the ambulatory fluid delivery device, the data including a patient basal medication dosage profile and device history logs;
  verify that the ambulatory fluid delivery device is compatible with a software update, including both verifying a memory capacity of the ambulatory fluid delivery device and confirming that a model of the ambulatory fluid delivery device is compatible with the software update;
  verify that a user of the ambulatory fluid delivery device wishes to update software on the ambulatory fluid delivery device;
  receive the software update from the central computing system;
  send the software update to the ambulatory fluid delivery device;
  verify that the ambulatory fluid delivery device is in a safe condition for the software update, including verifying an absence of error messages within a certain time period in the device history logs:
  receive confirmation that the software update has occurred on the ambulatory fluid delivery device; and
  verify that the ambulatory fluid delivery device is in a safe condition to perform as intended after the software update.

15. The system of claim 14, wherein the intermediate computing device is further programmed to:
  receive a password from the ambulatory fluid delivery device; and
  verify the password received from the ambulatory fluid delivery device with the central computing system.

16. The system of claim 14, wherein the intermediate computing device comprises a portable computing device.

17. The system of claim 14, where a safe condition for the software update comprises one or more of:
  the ambulatory fluid delivery device not currently administering a medicament,
  the ambulatory fluid delivery device not being attached to a patient, and
  a liquid medicament repository not being in fluid communication with the patient.

18. The system of claim 14, wherein verifying that the ambulatory fluid delivery device is in a safe condition to perform as intended after the software update comprises one or more of:
  verifying an ability of the ambulatory fluid delivery device to dispense one or more medicaments;
  verifying an ability of the ambulatory fluid delivery device to update a device history log; and
  verifying an ability of the ambulatory fluid delivery device to accept sensor data to influence medicament dosing.

19. The system of claim 14, wherein verifying a user of the ambulatory fluid delivery device wishes to update software on the ambulatory fluid delivery device includes receiving an indication of user input accepting a message pertaining to the software update.

20. The system of claim 14, wherein the intermediate computing device is programmed to verify that the ambulatory fluid delivery device is in a safe condition for the software update prior to sending the software update to the ambulatory fluid delivery device.

* * * * *

UNITED STATES PATENT AND TRADEMARK OFFICE
CERTIFICATE OF CORRECTION

PATENT NO. : 9,895,491 B2
APPLICATION NO. : 14/995958
DATED : February 20, 2018
INVENTOR(S) : Ludolph Page 1 of 1

It is certified that error appears in the above-identified patent and that said Letters Patent is hereby corrected as shown below:

On the Title Page

Item (73):
Delete "Diabeters" and insert -- Diabetes --

Signed and Sealed this
Twenty-fourth Day of July, 2018

Andrei Iancu
*Director of the United States Patent and Trademark Office*